(12) United States Patent
Grazulevicius et al.

(10) Patent No.: US 7,132,209 B2
(45) Date of Patent: Nov. 7, 2006

(54) ORGANOPHOTORECEPTOR WITH CHARGE TRANSPORT MATERIAL HAVING THREE ARYLAMINO GROUPS

(75) Inventors: Juozas Vidas Grazulevicius, Kaunas (LT); Gintaras Buika, Kaunas (LT); Vygintas Jankauskas, Vilnius (LT); Ruta Budreckiene, Kaunas (LT); Jonas Sidaravicius, Vilnius (LT); Zbigniew Tokarski, Woodbury, MN (US); Nusrallah Jubran, St. Paul, MN (US)

(73) Assignee: Samsung Electronics Co., Ltd, Kyungki-Do (KR)

( * ) Notice: Subject to any disclaimer, the term of this patent is extended or adjusted under 35 U.S.C. 154(b) by 287 days.

(21) Appl. No.: 10/699,581

(22) Filed: Oct. 31, 2003

(65) Prior Publication Data

US 2005/0095518 A1    May 5, 2005

(51) Int. Cl.
G03G 5/047 (2006.01)
C07D 209/82 (2006.01)

(52) U.S. Cl. ............................ 430/73; 430/78; 430/79; 430/117; 399/159; 546/95; 548/444; 564/251

(58) Field of Classification Search ................ 430/73, 430/79, 117, 970, 78; 546/95; 548/444; 399/159
See application file for complete search history.

(56) References Cited

U.S. PATENT DOCUMENTS

| | | | |
|---|---|---|---|
| 4,297,426 A | 10/1981 | Sakai et al. | |
| 4,786,571 A | 11/1988 | Ueda | |
| 5,942,615 A | 8/1999 | Kobayashi et al. | |
| 6,066,426 A | 5/2000 | Mott et al. | |
| 6,083,651 A | 7/2000 | Kobayashi et al. | |
| 6,140,004 A | 10/2000 | Mott et al. | |
| 6,214,503 B1 | 4/2001 | Gaidelis et al. | |
| 6,340,548 B1 * | 1/2002 | Jubran et al. | 430/58.45 |
| 6,670,085 B1 * | 12/2003 | Jubran et al. | 430/58.6 |
| 6,864,028 B1 * | 3/2005 | Jubran et al. | 430/73 |
| 2003/0232264 A1 | 12/2003 | Tokarski et al. | |

FOREIGN PATENT DOCUMENTS

DE  816923  7/1959

JP  2001-166519  6/2001

OTHER PUBLICATIONS

M. Daskeviciene et al., "Derivatives of 2,5-Dimercapto-1,3,4-thiazole as Hole Transporting Materials," Lithuanian Journal of Physics, 2001, 41, No. 4-6, 521-526.
"Synthesis, Characterization and Binding Properties of Epoxy Resins Based on Carbonohydrazones and Thiocarbonohydrazones", by P.M. Thangamathesvaran and S.R. Jain, Frontiers of Polymer Research, p. 589-594, Edited by P.N. Prasad and J.K. Nigam, Plenum Press, NY, 1991.
"Novel Energetic N-N Bonded Polymeric Binders for Composite Propellants," by S.R.Jain et el, Macromolecules New Frontiers, p. 1018-1021, Allied Publishers Ltd., New Delhi, 1998.

* cited by examiner

Primary Examiner—John L Goodrow
(74) Attorney, Agent, or Firm—Patterson, Thuente, Skaar & Christensen, PA

(57) ABSTRACT

Improved organophotoreceptor comprises an electrically conductive substrate and a photoconductive element on the electrically conductive substrate, the photoconductive element comprising:
(a) a charge transport material having the formula

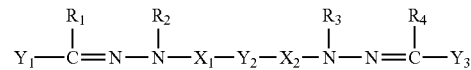

where $R_1$, $R_2$, $R_3$, and $R_4$ are, independently, H, an alkyl group, an alkaryl group, or an aryl group;
$X_1$ and $X_2$ are, independently, a linking group having the formula $-(CH_2)_m-$, branched or linear, where m is an integer between 1 and 20, inclusive, and one or more of the methylene groups is optionally replaced by O, S, C=O, O=S=O, a heterocyclic group, an aromatic group, urethane, urea, an ester group, a $NR_5$ group, a $CHR_6$ group, or a $CR_7R_8$ group where $R_4$, $R_5$, $R_6$, and $R_7$ are, independently, H, hydroxyl group, thiol group, an alkyl group, an alkaryl group, a heterocyclic group, or an aryl group; and
$Y_1$, $Y_2$, and $Y_3$ are, independently, an arylamine group; and
(b) a charge generating compound.

Corresponding electrophotographic apparatuses and imaging methods are described.

26 Claims, No Drawings

ORGANOPHOTORECEPTOR WITH CHARGE TRANSPORT MATERIAL HAVING THREE ARYLAMINO GROUPS

FIELD OF THE INVENTION

This invention relates to organophotoreceptors suitable for use in electrophotography and, more specifically, to organophotoreceptors having a charge transport material with three arylamino groups.

BACKGROUND OF THE INVENTION

In electrophotography, an organophotoreceptor in the form of a plate, disk, sheet, belt, drum or the like having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas where light strikes the surface, thereby forming a pattern of charged and uncharged areas, referred to as a latent image. A liquid or solid toner is then provided in the vicinity of the latent image, and toner droplets or particles deposit in the vicinity of either the charged or uncharged areas to create a toned image on the surface of the photoconductive layer. The resulting toned image can be transferred to a suitable ultimate or intermediate receiving surface, such as paper, or the photoconductive layer can operate as an ultimate receptor for the image. The imaging process can be repeated many times to complete a single image, for example, by overlaying images of distinct color components or effect shadow images, such as overlaying images of distinct colors to form a full color final image, and/or to reproduce additional images.

Both single layer and multilayer photoconductive elements have been used. In single layer embodiments, a charge transport material and charge generating material are combined with a polymeric binder and then deposited on the electrically conductive substrate. In multilayer embodiments, the charge transport material and charge generating material are present in the element in separate layers, each of which can optionally be combined with a polymeric binder, deposited on the electrically conductive substrate. Two arrangements are possible for a two-layer photoconductive element. In one two-layer arrangement (the "dual layer" arrangement), the charge-generating layer is deposited on the electrically conductive substrate and the charge transport layer is deposited on top of the charge generating layer. In an alternate two-layer arrangement (the "inverted dual layer" arrangement), the order of the charge transport layer and charge generating layer is reversed.

In both the single and multilayer photoconductive elements, the purpose of the charge generating material is to generate charge carriers (i.e., holes and/or electrons) upon exposure to light. The purpose of the charge transport material is to accept at least one type of these charge carriers and transport them through the charge transport layer in order to facilitate discharge of a surface charge on the photoconductive element. The charge transport material can be a charge transport compound, an electron transport compound, or a combination of both. When a charge transport compound is used, the charge transport compound accepts the hole carriers and transports them through the layer with the charge transport compound. When an electron transport compound is used, the electron transport compound accepts the electron carriers and transports them through the layer with the electron transport compound.

SUMMARY OF THE INVENTION

This invention provides organophotoreceptors having good electrostatic properties such as high $V_{acc}$ and low $V_{dis}$.

In a first aspect, an organophotoreceptor comprises an electrically conductive substrate and a photoconductive element on the electrically conductive substrate, the photoconductive element comprising:

(a) a charge transport material having the formula

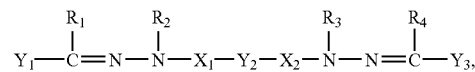

where $R_1$, $R_2$, $R_3$, and $R_4$ are, independently, H, an alkyl group, an alkaryl group, or an aryl group;

$X_1$ and $X_2$ are, independently, a linking group having the formula $-(CH_2)_m-$, branched or linear, where m is an integer between 1 and 20, inclusive, and one or more of the methylene groups is optionally replaced by O, S, C=O, O=S=O, a heterocyclic group, an aromatic group, urethane, urea, an ester group, a $NR_5$ group, a $CHR_6$ group, or a $CR_7R_8$ group where $R_4$, $R_5$, $R_6$, and $R_7$ are, independently, H, hydroxyl group, thiol group, an alkyl group, an alkaryl group, a heterocyclic group, or an aryl group; and $Y_1$, $Y_2$, and $Y_3$ are, independently, an arylamine group, such as a carbazole group, a julolidine group, or an (N,N-disubstituted)arylamine group; and (b) a charge generating compound.

The organophotoreceptor may be provided, for example, in the form of a plate, a flexible belt, a flexible disk, a sheet, a rigid drum, or a sheet around a rigid or compliant drum. In one embodiment, the organophotoreceptor includes: (a) a photoconductive element comprising the charge transport material, the charge generating compound, a second charge transport material, and a polymeric binder; and (b) the electrically conductive substrate.

In a second aspect, the invention features an electrophotographic imaging apparatus that comprises (a) a light imaging component; and (b) the above-described organophotoreceptor oriented to receive light from the light imaging component. The apparatus can further comprise a liquid toner dispenser. The method of electrophotographic imaging with photoreceptors containing the above noted charge transport materials is also described.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of at least relatively charged and uncharged areas on the surface; (c) contacting the surface with a toner, such as a liquid toner that includes a dispersion of colorant particles in an organic liquid, to create a toned image; and (d) transferring the toned image to a substrate.

In a fourth aspect, the invention features a charge transport material having the general formula above.

The invention provides suitable charge transport materials for organophotoreceptors featuring a combination of good mechanical and electrostatic properties. These photoreceptors can be used successfully with liquid toners to produce high quality images. The high quality of the imaging system can be maintained after repeated cycling.

Other features and advantages of the invention will be apparent from the following description of the particular embodiments thereof, and from the claims.

DETAILED DESCRIPTION OF PREFERRED EMBODIMENTS

An organophotoreceptor as described herein has an electrically conductive substrate and a photoconductive element comprising a charge generating compound and a charge transport material having three arylamine groups selected from the group consisting of a carbazole group, a julolidine group, or an (N,N-disubstituted)arylamine group. The three arylamine groups are linked together with two hydrazone groups and ether linkages. These charge transport materials can have desirable properties as evidenced by their performance in organophotoreceptors for electrophotography. In particular, the charge transport materials of this invention have high charge carrier mobilities and good compatibility with various binder materials, and possess excellent electrophotographic properties. The organophotoreceptors according to this invention generally have a high photosensitivity, a low residual potential, and a high stability with respect to cycle testing, crystallization, and organophotoreceptor bending and stretching. The organophotoreceptors are particularly useful in laser printers and the like as well as fax machines, photocopiers, scanners and other electronic devices based on electrophotography. The use of these charge transport materials is described in more detail below in the context of laser printer use, although their application in other devices operating by electrophotography can be generalized from the discussion below.

To produce high quality images, particularly after multiple cycles, it is desirable for the charge transport materials to form a homogeneous solution with the polymeric binder and remain approximately homogeneously distributed through the organophotoreceptor material during the cycling of the material. In addition, it is desirable to increase the amount of charge that the charge transport material can accept (indicated by a parameter known as the acceptance voltage or "$V_{acc}$"), and to reduce retention of that charge upon discharge (indicated by a parameter known as the discharge voltage or "$V_{dis}$").

The charge transport materials can be classified as a charge transport compound or an electron transport compound. There are many charge transport compounds and electron transport compounds known in the art for electrophotography. Non-limiting examples of charge transport compounds include, for example, pyrazoline derivatives, fluorene derivatives, oxadiazole derivatives, stilbene derivatives, enamine derivatives, enamine stilbene derivatives, hydrazone derivatives, carbazole hydrazone derivatives, (N,N-disubstituted)arylamine such as triaryl amines, polyvinyl carbazole, polyvinyl pyrene, polyacenaphthylene, or multi-hydrazone compounds comprising at least two hydrazone groups and at least two groups selected from the group consisting of (N,N-disubstituted)arylamine such as triphenylamine and heterocycles such as carbazole, julolidine, phenothiazine, phenazine, phenoxazine, phenoxathiin, thiazole, oxazole, isoxazole, dibenzo(1,4)dioxin, thianthrene, imidazole, benzothiazole, benzotriazole, benzoxazole, benzimidazole, quinoline, isoquinoline, quinoxaline, indole, indazole, pyrrole, purine, pyridine, pyridazine, pyrimidine, pyrazine, triazole, oxadiazole, tetrazole, thiadiazole, benzisoxazole, benzisothiazole, dibenzofuran, dibenzothiophene, thiophene, thianaphthene, quinazoline, or cinnoline.

Non-limiting examples of electron transport compounds include, for example, bromoaniline, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-indeno4H-indeno[1,2-b]thiophene-4-one, and 1,3,7-trinitrodibenzo thiophene-5,5-dioxide, (2,3-diphenyl-1-indenylidene)malononitrile, 4H-thiopyran-1,1-dioxide and its derivatives such as 4-dicyanomethylene-2,6-diphenyl-4H-thiopyran-1,1-dioxide, 4-dicyanomethylene-2,6-di-m-tolyl-4H-thiopyran-1,1-dioxide, and unsymmetrically substituted 2,6-diaryl-4H-thiopyran-1,1-dioxide such as 4H-1,1-dioxo-2-(p-isopropylphenyl)-6-phenyl-4-(dicyanomethylidene)thiopyran and 4H-1,1-dioxo-2-(p-isopropylphenyl)-6-(2-thienyl)-4-(dicyanomethylidene)thiopyran, derivatives of phospha-2,5-cyclohexadiene, alkoxycarbonyl-9-fluorenylidene)malononitrile derivatives such as (4-n-butoxycarbonyl-9-fluorenylidene)malononitrile, (4-phenethoxycarbonyl-9-fluorenylidene)malononitrile, (4-carbitoxy-9-fluorenylidene)malononitrile, and diethyl(4-n-butoxycarbonyl-2,7-dinitro-9-fluorenylidene)-malonate, anthraquinodimethane derivatives such as 11,11,12,12-tetracyano-2-alkylanthraquinodimethane and 11,11-dicyano-12,12-bis(ethoxycarbonyl)anthraquinodimethane, anthrone derivatives such as 1-chloro-10-[bis(ethoxycarbonyl)methylene]anthrone, 1,8-dichloro-10-[bis(ethoxy carbonyl)methylene]anthrone, 1,8-dihydroxy-10-[bis(ethoxycarbonyl)methylene]anthrone, and 1-cyano-10-[bis(ethoxycarbonyl)methylene)anthrone, 7-nitro-2-aza-9-fluroenylidene-malononitrile, diphenoquinone derivatives, benzoquinone derivatives, naphtoquinone derivatives, quinine derivatives, tetracyanoethylenecyanoethylene, 2,4,8-trinitro thioxantone, dinitrobenzene derivatives, dinitroanthracene derivatives, dinitroacridine derivatives, nitroanthraquinone derivatives, dinitroanthraquinone derivatives, succinic anhydride, maleic anhydride, dibromo maleic anhydride, pyrene derivatives, carbazole derivatives, hydrazone derivatives, N,N-dialkylaniline derivatives, diphenylamine derivatives, triphenylamine derivatives, triphenylmethane derivatives, tetracyano quinoedimethane, 2,4,5,7-tetranitro-9-fluorenone, 2,4,7-trinitro-9-dicyanomethylene fluorenone, 2,4,5,7-tetranitroxanthone derivatives, and 2,4,8-trinitrothioxanthone derivatives. In some embodiments of interest, the electron transport compound comprises an (alkoxycarbonyl-9-fluorenylidene)malononitrile derivative, such as (4-n-butoxycarbonyl-9-fluorenylidene)malononitrile.

Although there are many charge transport materials available, there is a need for other charge transport materials to meet the various requirements of particular electrophotography applications.

In electrophotography applications, a charge-generating compound within an organophotoreceptor absorbs light to form electron-hole pairs. These electrons and holes can be transported over an appropriate time frame under a large electric field to discharge locally a surface charge that is generating the field. The discharge of the field at a particular location results in a surface charge pattern that essentially matches the pattern drawn with the light. This charge pattern then can be used to guide toner deposition. The charge transport materials described herein are especially effective at transporting charge, and in particular holes from the electron-hole pairs formed by the charge generating compound. In some embodiments, a specific electron transport compound or charge transport compound can also be used along with the charge transport material described herein with three arylamine groups.

The layer or layers of materials containing the charge generating compound and the charge transport materials are within an organophotoreceptor. To print a two dimensional image using the organophotoreceptor, the organophotoreceptor has a two dimensional surface for forming at least a portion of the image. The imaging process then continues by cycling the organophotoreceptor to complete the formation of the entire image and/or for the processing of subsequent images.

The organophotoreceptor may be provided in the form of a plate, a flexible belt, a disk, a rigid drum, a sheet around a rigid or compliant drum, or the like. The charge transport material can be in the same layer as the charge generating compound and/or in a different layer from the charge generating compound. Additional layers can be used also, as described further below.

In some embodiments, the organophotoreceptor material comprises, for example: (a) a charge transport layer comprising the charge transport material and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate. In further embodiments, the organophotoreceptor material has a single layer with both a charge transport material and a charge generating compound within a polymeric binder.

The organophotoreceptors can be incorporated into an electrophotographic imaging apparatus, such as laser printers. In these devices, an image is formed from physical embodiments and converted to a light image that is scanned onto the organophotoreceptor to form a surface latent image. The surface latent image can be used to attract toner onto the surface of the organophotoreceptor, in which the toner image is the same or the negative of the light image projected onto the organophotoreceptor. The toner can be a liquid toner or a dry toner. The toner is subsequently transferred, from the surface of the organophotoreceptor, to a receiving surface, such as a sheet of paper. After the transfer of the toner, the entire surface is discharged, and the material is ready to cycle again. The imaging apparatus can further comprise, for example, a plurality of support rollers for transporting a paper receiving medium and/or for movement of the photoreceptor, a light imaging component with suitable optics to form the light image, a light source, such as a laser, a toner source and delivery system and an appropriate control system.

An electrophotographic imaging process generally can comprise (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) exposing the surface with a toner, such as a liquid toner that includes a dispersion of colorant particles in an organic liquid to create a toner image, to attract toner to the charged or discharged regions of the organophotoreceptor; and (d) transferring the toner image to a substrate.

As described herein, an organophotoreceptor comprises a charge transport material having the formula

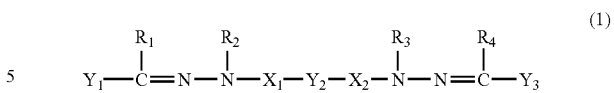

where $R_1$, $R_2$, $R_3$, and $R_4$ are, independently, H, an alkyl group, an alkaryl group, or an aryl group;

$X_1$ and $X_2$ are, independently, a linking group having the formula $-(CH_2)_m-$, branched or linear, where m is an integer between 1 and 20, inclusive, and one or more of the methylene groups is optionally replaced by O, S, C=O, O=S=O, a heterocyclic group, an aromatic group, urethane, urea, an ester group, a $NR_5$ group, a $CHR_6$ group, or a $CR_7R_8$ group where $R_4$, $R_5$, $R_6$, and $R_7$ are, independently, H, hydroxyl group, thiol group, an alkyl group, an alkaryl group, a heterocyclic group, or an aryl group; and $Y_1$, $Y_2$, and $Y_3$ are, independently, an arylamine group, such as a carbazole group, a julolidine group, or an (N,N-disubstituted)arylamine group.

Substitution is liberally allowed on the chemical groups to affect various physical effects on the properties of the compounds, such as mobility, sensitivity, solubility, stability, and the like, as is known generally in the art. In the description of chemical substituents, there are certain practices common to the art that are reflected in the use of language. The term group indicates that the generically recited chemical entity (e.g., alkyl group, alkaryl group, aryl group, phenyl group, carbazole group, julolidine group, or (N,N-disubstituted)arylamine group, etc.) may have any substituent thereon which is consistent with the bond structure of that group. For example, where the term 'alkyl group' is used, that term would not only include unsubstituted liner, branched and cyclic alkyls, such as methyl, ethyl, isopropyl, tert-butyl, cyclohexyl, dodecyl and the like, but also substituents such as hydroxyethyl, cyanobutyl, 1,2,3-trichloropropane, and the like. However, as is consistent with such nomenclature, no substitution would be included within the term that would alter the fundamental bond structure of the underlying group. For example, where a phenyl group is recited, substitution such as 1-hydroxyphenyl, 2,4-fluorophenyl, orthocyanophenyl, 1,3,5-trimethoxyphenyl and the like would be acceptable within the terminology, while substitution of 1,1,2,2,3,3-hexamethylphenyl would not be acceptable as that substitution would require the ring bond structure of the phenyl group to be altered to a non-aromatic form because of the substitution. Where the term moiety is used, such as alkyl moiety or phenyl moiety, that terminology indicates that the chemical material is not substituted. Where the term alkyl moiety is used, that term represents only an unsubstituted alkyl hydrocarbon group, whether branched, straight chain, or cyclic.

Organophotoreceptors

The organophotoreceptor may be, for example, in the form of a plate, a sheet, a flexible belt, a disk, a rigid drum, or a sheet around a rigid or compliant drum, with flexible belts and rigid drums generally being used in commercial embodiments. The organophotoreceptor may comprise, for example, an electrically conductive substrate and on the electrically conductive substrate a photoconductive element in the form of one or more layers. The photoconductive element can comprise both a charge transport material and a charge generating compound in a polymeric binder, which may or may not be in the same layer, as well as a second charge transport material such as a charge transport compound or an electron transport compound in some embodiments. For example, the charge transport material and the charge generating compound can be in a single layer. In other embodiments, however, the photoconductive element comprises a bilayer construction featuring a charge generating layer and a separate charge transport layer. The charge generating layer may be located intermediate between the electrically conductive substrate and the charge transport layer. Alternatively, the photoconductive element may have a structure in which the charge transport layer is intermediate between the electrically conductive substrate and the charge generating layer.

The electrically conductive substrate may be flexible, for example in the form of a flexible web or a belt, or inflexible, for example in the form of a drum. A drum can have a hollow cylindrical structure that provides for attachment of the drum to a drive that rotates the drum during the imaging process. Typically, a flexible electrically conductive substrate comprises an electrically insulating substrate and a thin layer of electrically conductive material onto which the photoconductive material is applied.

The electrically insulating substrate may be paper or a film forming polymer such as polyester (e.g., polyethylene terephthalate or polyethylene naphthalate), polyimide, polysulfone, polypropylene, nylon, polyester, polycarbonate, polyvinyl resin, polyvinyl fluoride, polystyrene and the like. Specific examples of polymers for supporting substrates included, for example, polyethersulfone (Stabar™ S-100, available from ICI), polyvinyl fluoride (Tedlar®, available from E.I. DuPont de Nemours & Company), polybisphenol-A polycarbonate (Makrofol™, available from Mobay Chemical Company) and amorphous polyethylene terephthalate (Melinar™, available from ICI Americas, Inc.). The electrically conductive materials may be graphite, dispersed carbon black, iodine, conductive polymers such as polypyroles and Calgon® conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. In embodiments of particular interest, the electrically conductive material is aluminum. Generally, the photoconductor substrate has a thickness adequate to provide the required mechanical stability. For example, flexible web substrates generally have a thickness from about 0.01 to about 1 mm, while drum substrates generally have a thickness from about 0.5 mm to about 2 mm.

The charge generating compound is a material that is capable of absorbing light to generate charge carriers, such as a dye or pigment. Non-limiting examples of suitable charge generating compounds include, for example, metal-free phthalocyanines (e.g., ELA 8034 metal-free phthalocyanine available from H.W. Sands, Inc. or Sanyo Color Works, Ltd., CGM-X01), metal phthalocyanines such as titanium phthalocyanine, copper phthalocyanine, oxytitanium phthalocyanine (also referred to as titanyl oxyphthalocyanine, and including any crystalline phase or mixtures of crystalline phases that can act as a charge generating compound), hydroxygallium phthalocyanine, squarylium dyes and pigments, hydroxy-substituted squarylium pigments, perylimides, polynuclear quinones available from Allied Chemical Corporation under the tradename Indofast® Double Scarlet, Indofast® Violet Lake B, Indofast® Brilliant Scarlet and Indofast® Orange, quinacridones available from DuPont under the tradename Monastral™ Red, Monastral™ Violet and Monastral™ Red Y, naphthalene 1,4,5,8-tetracarboxylic acid derived pigments including the perinones, tetrabenzoporphyrins and tetranaphthaloporphyrins, indigo- and thioindigo dyes, benzothioxanthene-derivatives, perylene 3,4,9,10-tetracarboxylic acid derived pigments, polyazo-pigments including bisazo-, trisazo- and tetrakisazo-pigments, polym-ethine dyes, dyes containing quinazoline groups, tertiary amines, amorphous selenium, selenium alloys such as selenium-tellurium, selenium-tellurium-arsenic and selenium-arsenic, cadmium sulphoselenide, cadmium selenide, cadmium sulphide, and mixtures thereof. For some embodiments, the charge generating compound comprises oxytitanium phthalocyanine (e.g., any phase thereof), hydroxygallium phthalocyanine or a combination thereof.

The photoconductive layer of this invention may optionally contain a second charge transport material which may be a charge transport compound, an electron transport compound, or a combination of both. Generally, any charge transport compound or electron transport compound known in the art can be used as the second charge transport material.

An electron transport compound and a UV light stabilizer can have a synergistic relationship for providing desired electron flow within the photoconductor. The presence of the UV light stabilizers alters the electron transport properties of the electron transport compounds to improve the electron transporting properties of the composite. UV light stabilizers can be ultraviolet light absorbers or ultraviolet light inhibitors that trap free radicals.

UV light absorbers can absorb ultraviolet radiation and dissipate it as heat. UV light inhibitors are thought to trap free radicals generated by the ultraviolet light and after trapping of the free radicals, subsequently to regenerate active stabilizer moieties with energy dissipation. In view of the synergistic relationship of the UV stabilizers with electron transport compounds, the particular advantages of the UV stabilizers may not be their UV stabilizing abilities, although the UV stabilizing ability may be further advantageous in reducing degradation of the organophotoreceptor over time. The improved synergistic performance of organophotoreceptors with layers comprising both an electron transport compound and a UV stabilizer are described further in copending U.S. patent application Ser. No. 10/425,333 filed on Apr. 28, 2003 to Zhu, entitled "Organophotoreceptor With A Light Stabilizer," incorporated herein by reference.

Non-limiting examples of suitable light stabilizer include, for example, hindered trialkylamines such as Tinuvin 144 and Tinuvin 292 (from Ciba Specialty Chemicals, Terrytown, N.Y.), hindered alkoxydialkylamines such as Tinuvin 123 (from Ciba Specialty Chemicals), benzotriazoles such as Tinuvan 328, Tinuvin 900 and Tinuvin 928 (from Ciba Specialty Chemicals), benzophenones such as Sanduvor 3041 (from Clariant Corp., Charlotte, N.C.), nickel compounds such as Arbestab (from Robinson Brothers Ltd, West Midlands, Great Britain), salicylates, cyanocinnamates, benzylidene malonates, benzoates, oxanilides such as Sanduvor VSU (from Clariant Corp., Charlotte, N.C.), triazines such as Cyagard UV-1164 (from Cytec Industries Inc., N.J.), polymeric sterically hindered amines such as Luchem (from Atochem North America, Buffalo, N.Y.). In some embodiments, the light stabilizer is selected from the group consisting of hindered trialkylamines having the following formula:

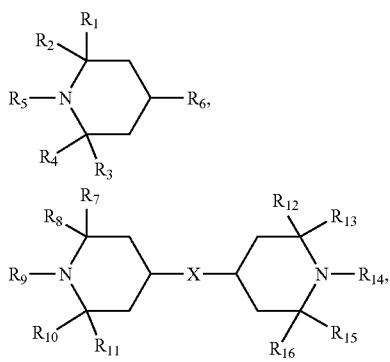

where $R_1$, $R_2$, $R_3$, $R_4$, $R_6$, $R_7$, $R_8$, $R_{10}$, $R_{11}$, $R_{12}$, $R_{13}$, $R_{14}$, $R_{15}$ are, indeoendently, hydrogen, alkyl group, or ester, or ether group; and $R_5$, $R_9$, and $R_{14}$ are, independently, alkyl group; and X is a linking group selected from the group consisting of —O—CO—$(CH_2)_m$—CO—O—where m is between 2 to 20.

The binder generally is capable of dispersing or dissolving the charge transport material (in the case of the charge transport layer or a single layer construction), the charge generating compound (in the case of the charge generating layer or a single layer construction) and/or an electron transport compound for appropriate embodiments. Examples of suitable binders for both the charge generating layer and charge transport layer generally include, for example, polystyrene-co-butadiene, polystyrene-co-acrylonitrile, modified acrylic polymers, polyvinyl acetate, styrene-alkyd resins, soya-alkyl resins, polyvinylchloride, polyvinylidene chloride, polyacrylonitrile, polycarbonates, polyacrylic acid, polyacrylates, polymethacrylates, styrene polymers, polyvinyl butyral, alkyd resins, polyamides, polyurethanes, polyesters (e.g. polyethylene terephthalate), polysulfones, polyethers, polyketones, phenoxy resins, epoxy resins, silicone resins, polysiloxanes, poly(hydroxyether) resins, polyhydroxystyrene resins, novolak, poly(phenylglycidyl ether)-co-dicyclopentadiene, copolymers of monomers used in the above-mentioned polymers, and combinations thereof. Specific suitable binders include, for example, polyvinyl butyral, polycarbonate, and polyester. Non-limiting examples of polyvinyl butyral include BX-1 and BX-5 from Sekisui Chemical Co. Ltd., Japan. Non-limiting examples of suitable polycarbonate include polycarbonate A which is derived from bisphenol-A (e.g. Iupilon-A from Mitsubishi Engineering Plastics, or Lexan 145 from General Electric); polycarbonate Z which is derived from cyclohexylidene bisphenol (e.g. Iupilon-Z from Mitsubishi Engineering Plastics Corp, White Plain, N.Y.); and polycarbonate C which is derived from methylbisphenol A (from Mitsubishi Chemical Corporation). Non-limiting examples of suitable polyester binders include ortho-polyethylene terephthalate (e.g. OPET TR-4 from Kanebo Ltd., Yamaguchi, Japan).

Suitable optional additives for any one or more of the layers include, for example, antioxidants, coupling agents, dispersing agents, curing agents, surfactants, and combinations thereof.

The photoconductive element overall typically has a thickness from about 10 to about 45 microns. In the dual layer embodiments having a separate charge generating layer and a separate charge transport layer, charge generation layer generally has a thickness form about 0.5 to about 2 microns, and the charge transport layer has a thickness from about 5 to about 35 microns. In embodiments in which the charge transport material and the charge generating compound are in the same layer, the layer with the charge generating compound and the charge transport composition generally has a thickness from about 7 to about 30 microns. In embodiments with a distinct electron transport layer, the electron transport layer has an average thickness from about 0.5 microns to about 10 microns and in further embodiments from about 1 micron to about 3 microns. In general, an electron transport overcoat layer can increase mechanical abrasion resistance, increases resistance to carrier liquid and atmospheric moisture, and decreases degradation of the photoreceptor by corona gases. A person of ordinary skill in the art will recognize that additional ranges of thickness within the explicit ranges above are contemplated and are within the present disclosure.

Generally, for the organophotoreceptors described herein, the charge generation compound is in an amount from about 0.5 to about 25 weight percent, in further embodiments in an amount from about 1 to about 15 weight percent and in other embodiments in an amount from about 2 to about 10 weight percent, based on the weight of the photoconductive layer. The charge transport material is in an amount from about 10 to about 80 weight percent, based on the weight of the photoconductive layer, in further embodiments in an amount from about 35 to about 60 weight percent, and in other embodiments from about 45 to about 55 weight percent, based on the weight of the photoconductive layer. The optional second charge transport material, when present, can be in an amount of at least about 2 weight percent, in other embodiments from about 2.5 to about 25 weight percent, based on the weight of the photoconductive layer, and in further embodiments in an amount from about 4 to about 20 weight percent, based on the weight of the photoconductive layer. The binder is in an amount from about 15 to about 80 weight percent, based on the weight of the photoconductive layer, and in further embodiments in an amount from about 20 to about 75 weight percent, based on the weight of the photoconductive layer. A person of ordinary skill in the art will recognize that additional ranges within the explicit ranges of compositions are contemplated and are within the present disclosure.

For the dual layer embodiments with a separate charge generating layer and a charge transport layer, the charge generation layer generally comprises a binder in an amount from about 10 to about 90 weight percent, in further embodiments from about 15 to about 80 weight percent and in some embodiments in an amount from about 20 to about 75 weight percent, based on the weight of the charge generation layer. The optional charge transport material in the charge generating layer, if present, generally can be in an amount of at least about 2.5 weight percent, in further embodiments from about 4 to about 30 weight percent and in other embodiments in an amount from about 10 to about 25 weight percent, based on the weight of the charge generating layer.

The charge transport layer generally comprises a binder in an amount from about 20 weight percent to about 70 weight percent and in further embodiments in an amount from about 30 weight percent to about 50 weight percent. A person of ordinary skill in the art will recognize that additional ranges of binder concentrations for the dual layer embodiments within the explicit ranges above are contemplated and are within the present disclosure.

For the embodiments with a single layer having a charge generating compound and a charge transport material, the photoconductive layer generally comprises a binder, a charge transport material, and a charge generation compound. The charge generation compound can be in an amount from about 0.05 to about 25 weight percent and in further embodiment in an amount from about 2 to about 15 weight percent, based on the weight of the photoconductive layer. The charge transport material can be in an amount from about 10 to about 80 weight percent, in other embodiments from about 25 to about 65 weight percent, in additional embodiments from about 30 to about 60 weight percent and in further embodiments in an amount from about 35 to about 55 weight percent, based on the weight of the photoconductive layer, with the remainder of the photoconductive layer comprising the binder, and optionally additives, such as any conventional additives. A single layer with a charge transport composition and a charge generating compound generally comprises a binder in an amount from about 10 weight percent to about 75 weight percent, in other embodiments from about 20 weight percent to about 60 weight percent, and in further embodiments from about 25 weight percent to about 50 weight percent. Optionally, the layer with the charge generating compound and the charge transport material may comprise a second charge transport material. The optional second charge transport material, if present, generally can be in an amount of at least about 2.5 weight percent, in further embodiments from about 4 to about 30 weight percent and in other embodiments in an amount from about 10 to about 25 weight percent, based on the weight of the photoconductive layer. A person of ordinary skill in the art will recognize that additional composition ranges within the explicit compositions ranges for the layers above are contemplated and are within the present disclosure.

In general, any layer with an electron transport layer can advantageously further include a UV light stabilizer. In particular, the electron transport layer generally can comprise an electron transport compound, a binder, and an optional UV light stabilizer. An overcoat layer comprising an electron transport compound is described further in copending U.S. patent application Ser. No. 10/396,536 to Zhu et al. entitled, "Organophotoreceptor With An Electron Transport Layer," incorporated herein by reference. For example, an electron transport compound as described above may be used in the release layer of the photoconductors described herein. The electron transport compound in an electron transport layer can be in an amount from about 10 to about 50 weight percent, and in other embodiments in an amount from about 20 to about 40 weight percent, based on the weight of the electron transport layer. A person of ordinary skill in the art will recognize that additional ranges of compositions within the explicit ranges are contemplated and are within the present disclosure.

The UV light stabilizer, if present, in any one or more appropriate layers of the photoconductor generally is in an amount from about 0.5 to about 25 weight percent and in some embodiments in an amount from about 1 to about 10 weight percent, based on the weight of the particular layer. A person of ordinary skill in the art will recognize that additional ranges of compositions within the explicit ranges are contemplated and are within the present disclosure.

For example, the photoconductive layer may be formed by dispersing or dissolving the components, such as one or more of a charge generating compound, the charge transport material of this invention, a second charge transport material such as a charge transport compound or an electron transport compound, a UV light stabilizer, and a polymeric binder in organic solvent, coating the dispersion and/or solution on the respective underlying layer and drying the coating. In particular, the components can be dispersed by high shear homogenization, ball-milling, attritor milling, high energy bead (sand) milling or other size reduction processes or mixing means known in the art for effecting particle size reduction in forming a dispersion.

The photoreceptor may optionally have one or more additional layers as well. An additional layer can be, for example, a sub-layer or an overcoat layer, such as a barrier layer, a release layer, a protective layer, or an adhesive layer. A release layer or a protective layer may form the uppermost layer of the photoconductor element. A barrier layer may be sandwiched between the release layer and the photoconductive element or used to overcoat the photoconductive element. The barrier layer provides protection from abrasion to the underlayers. An adhesive layer locates and improves the adhesion between a photoconductive element, a barrier layer and a release layer, or any combination thereof. A sub-layer is a charge blocking layer and locates between the electrically conductive substrate and the photoconductive element. The sub-layer may also improve the adhesion between the electrically conductive substrate and the photoconductive element.

Suitable barrier layers include, for example, coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyvinyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above barrier layer polymers optionally may contain small inorganic particles such as fumed silica, silica, titania, alumina, zirconia, or a combination thereof. Barrier layers are described further in U.S. Pat. No. 6,001,522 to Woo et al., entitled "Barrier Layer For Photoconductor Elements Comprising An Organic Polymer And Silica," incorporated herein by reference. The release layer topcoat may comprise any release layer composition known in the art. In some embodiments, the release layer is a fluorinated polymer, siloxane polymer, fluorosilicone polymer, silane, polyethylene, polypropylene, polyacrylate, or a combination thereof. The release layers can comprise crosslinked polymers.

The release layer may comprise, for example, any release layer composition known in the art. In some embodiments, the release layer comprises a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof In further embodiments, the release layers comprise crosslinked polymers.

The protective layer can protect the organophotoreceptor from chemical and mechanical degradation. The protective layer may comprise any protective layer composition known in the art. In some embodiments, the protective layer is a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In some embodiments of particular interest, the release layers are crosslinked polymers.

An overcoat layer may comprise an electron transport compound as described further in copending U.S. patent application Ser. No. 10/396,536, filed on Mar. 25, 2003 to Zhu et al. entitled, "Organoreceptor With An Electron Transport Layer," incorporated herein by reference. For example, an electron transport compound, as described above, may be used in the release layer of this invention. The electron transport compound in the overcoat layer can be in an amount from about 2 to about 50 weight percent, and in other embodiments in an amount from about 10 to about 40 weight percent, based on the weight of the release layer. A person of ordinary skill in the art will recognize that additional ranges of composition within the explicit ranges are contemplated and are within the present disclosure.

Generally, adhesive layers comprise a film forming polymer, such as polyester, polyvinylbutyral, polyvinylpyrolidone, polyurethane, polymethyl methacrylate, poly(hydroxy amino ether) and the like. Barrier and adhesive layers are described further in U.S. Pat. No. 6,180,305 to Ackley et al., entitled "Organic Photoreceptors for Liquid Electrophotography," incorporated herein by reference.

Sub-layers can comprise, for example, polyvinylbutyral, organosilanes, hydrolyzable silanes, epoxy resins, polyesters, polyamides, polyurethanes, silicones, and the like. In some embodiments, the sub-layer has a dry thickness between about 20 Angstroms and about 2,000 Angstroms. Sublayers containing metal oxide conductive particles can be between about 1 and about 25 microns thick. A person of ordinary skill in the art will recognize that additional ranges of compositions and thickness within the explicit ranges are contemplated and are within the present disclosure.

The charge transport materials as described herein, and photoreceptors including these compounds, are suitable for use in an imaging process with either dry or liquid toner development. For example, any dry toners and liquid toners known in the art may be used in the process and the apparatus of this invention. Liquid toner development can be desirable because it offers the advantages of providing higher resolution images and requiring lower energy for image fixing compared to dry toners. Examples of suitable liquid toners are known in the art. Liquid toners generally comprise toner particles dispersed in a carrier liquid. The toner particles can comprise a colorant/pigment, a resin binder, and/or a charge director. In some embodiments of liquid toner, a resin to pigment ratio can be from 1:1 to 10:1, and in other embodiments, from 4:1 to 8:1. Liquid toners are described further in Published U.S. Patent Applications 2002/0128349, entitled "Liquid Inks Comprising A Stable Organosol," 2002/0086916, entitled "Liquid Inks Comprising Treated Colorant Particles," and 2002/0197552, entitled "Phase Change Developer For Liquid Electrophotography," all three of which are incorporated herein by reference.

Charge Transport Material

As described herein, an organophotoreceptor comprises a charge transport material having the formula

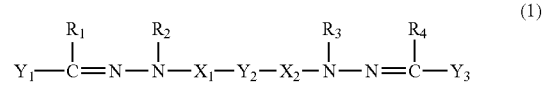

(1)

where $R_1$, $R_2$, $R_3$, and $R_4$ are, independently, H, an alkyl group, an alkaryl group, or an aryl group;

$X_1$ and $X_2$ are, independently, a linking group having the formula $-(CH_2)_m-$, branched or linear, where m is an integer between 1 and 20, inclusive, and one or more of the methylene groups is optionally replaced by O, S, C=O, O=S=O, a heterocyclic group, an aromatic group, urethane, urea, an ester group, a $NR_5$ group, a $CHR_6$ group, or a $CR_7R_8$ group where $R_4$, $R_5$, $R_6$, and $R_7$ are, independently, H, hydroxyl group, thiol group, an alkyl group, an alkaryl group, a heterocyclic group, or an aryl group; and $Y_1$, $Y_2$, and $Y_3$ are, independently, an arylamine group, such as a carbazole group, a julolidine group, or an (N,N-disubstituted)arylamine group.

Specific, non-limiting examples of suitable charge transport materials within the general Formula (1) of the present invention have the following structures

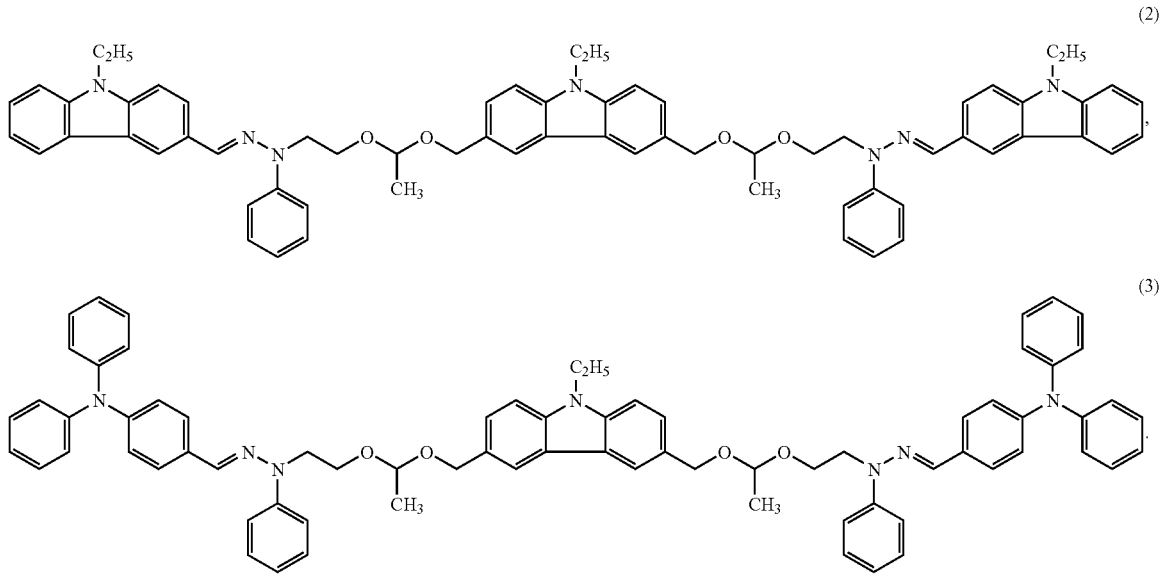

Synthesis of Charge Transport Materials

The synthesis of the charge transport materials of this invention can be prepared by the following multi-step synthetic procedure. A person of ordinary skill in the art will recognize that other appropriate synthesis approaches can be substituted for the particular approach described below.

Step 1: Monoformylation of the Arylamine

In this step, the arylamine that forms the $Y_1$ or $Y_3$ group of Formula (1) is reacted to be formyl substituted such that it will react with a hydrazine to form a hydrozone. Phosphorus oxychloride ($POCl_3$) is added dropwise to dry dimethylformamide (DMF) at 0° C. under a nitrogen atmosphere. This solution is warmed up slowly to room temperature. A solution of a selected arylamine in dry DMF can be added dropwise to this solution. The reaction mixture is heated at 80° C. for 24 hours and poured into ice water. This solution is neutralized with 10% potassium hydroxide solution until the pH value reaches 6–8. The product can be extracted with chloroform. The chloroform extract is dried with anhydrous sodium sulfate and filtered Then, the solvent is evaporated. The product is an aldehyde of the arylamine, which can be crystallized from a solvent such as methanol. A substituted form of dimethyl formamide can be used to form a corresponding ketone, which would result in a compound with $R_1$ (for the $Y_1$ arylamine) or $R_4$ (for the $Y_3$ arylamine) of Formula (1) being different from hydrogen.

Step 2: Hydrazone Formation

The aldehyde or ketone of the arylamine obtained in Step 1 above is dissolved in methanol under mild heating. A solution of an N-substituted-hydrazine in methanol is added to the solution. The reaction mixture is refluxed for 2 hours and then slowly cooled down to room temperature. The precipitated product is a hydrazone derivative of the aldehyde/ketone of the arylamine. The hydrazone derivative is filtered, washed with a large amount of methanol, and then vacuum dried at room temperature, e.g., using a high vacuum oil pump.

Step 3: Reaction of Hydrazone with 2-Chloroalkyl vinyl ether

The hydrazone derivative obtained in Step 2 is dissolved in ethyl methyl ketone to form a solution and then 2-chloroalkyl vinyl ether is added to the solution. Later potassium hydroxide (KOH) and potassium carbonate ($K_2CO_3$) are added in two portions into the reaction mixture. The reaction mixture is refluxed for 36 hours. The product is an arylaminocarbaldehyde-N-(vinyloxyalkyl)-hydrazone and can be purified by column chromatography. Other halogen-substitued vinyl ethers compounds can be used to introduce other X ($X_1$ or $X_2$) groups into the resulting charge transport materials of Formula (1).

Step 4. Diformylation of an Arylamine

In this step, the $Y_2$ group is prepared for bonding to the $X_1/X_2$ linkers. Phosphorus oxychloride ($POCl_3$) is added dropwise to dry dimethylformamide (DMF) at 0° C. under a nitrogen atmosphere to form a solution. The solution is warmed up slowly to room temperature. A solution of an arylamine in dry DMF is added dropwise to the solution. The reaction mixture is heated at 80° C. for 60 hours. It is then cooled to room temperature and poured into ice water. The mixture is neutralized with 10% potassium hydroxide solution until the pH reaches 6–8. The precipitate is filtrated and washed several times with hot water. The product is a diformylarylamine and can be purified by column chromatography.

Step 5. Reduction of a Diformylarylamine

Small portions of sodium borohydride are slowly added into a solution of the diformylarylamine in methanol, and the reaction mixture is refluxed for 2 hours. The reaction mixture is cooled down and then poured into ice water. The precipitated product is a dihydroxymethylarylamine which can be separated by filtration and then dried.

Step 6. Coupling of Dihydroxymethylarylamine with Arylaminocarbaldehyde-N-(vinyloxyalkyl)-hydrazone In this step, the dihydroxymethylarylamine of step 5 is bonded to the $X_1$ and $X_2$ linking groups. The arylaminocarbaldehyde/ketone-N-(vinyloxyalkyl)-hydrazone, obtained in Step 3, and a corresponding approximately half mole equivalent of dihydroxymethylarylamine, obtained in Step 5, are dissolved in dry tetrahydrofuran (THF) under nitrogen. Then, p-toluenesulfonic anhydride solution in dry THF is added to the solution at room temperature. The reaction mixture is stirred at 0° C. for 18 hours. Then THF is evaporated, and the crude product can be purified by column chromatography. As described above, a symmetric compound is formed with $Y_1=Y_3$, $X_1=X_2$, $R_1=R_4$ and $R_2=R_3$. An unsymmetric compound can be synthesized with two different arylaminocarbaldehyde/ketone-N-(vinyloxyalkyl)-hydrazone synthesized as described in steps 1–3 with different selected arylamines in step 1. The two different arylaminocarbaldehyde/ketone-N-(vinyloxyalkyl)-hydrazone compounds can be reacted sequentially or simultaneously with the dihydroxylmethylarylamine of step 5. The reaction condictions can be selected to form a significant fraction of the unsymmetric compound relative to the two possible symmetric compounds. Furthermore, the unsymmetric compound can purified from the symmetric compounds.

The invention will now be described further by way of the following examples.

EXAMPLES

Example 1

Synthesis and Characterization Charge Transport Materials

This example described the synthesis and characterization of Compounds 2–3 in which the numbers refer to formula numbers above. The characterization involves both chemical characterization and the electronic characterization of materials formed with the compound.

Compound (2)

$POCl_3$ (4.8 ml, 0.052 mol) (obtained from Aldrich) was added dropwise to 5.7 ml (0.078 mol) of dry dimethylformamide (DMF) at 0° C. under a nitrogen atmosphere. The solution was warmed up slowly to room temperature. Then, a solution of 5 g (0.026 mol) of 9-ethylcarbazole (obtained from Aldrich) in dry DMF was added dropwise to the solution. The reaction mixture was heated at 80° C. for 24 hours and then poured into ice water. This solution was neutralized with 10% solution of potassium hydroxide until the pH reached 6–8. The product was extracted with chloroform. The chloroform extract was dried with anhydrous sodium sulfate and filtered. The solvent was removed from the filtrate with a rotary evaporator. The product was 9-ethylcarbazole-3-carbaldehyde and was recrystallized from methanol. The yield was 4.57 g (80%). The product had a melting point of 85° C. A $^1H$ NMR spectrum yielded the following chemical shifts (100 MHz, $CDCl_3$, δ, ppm): 1.42 (t, J=7.0 Hz, 3H, $CH_3$); 4.31 (q, J=7.0 Hz, 2H, $CH_2$); 7.20–7.62 (m, 4H, Ar); 7.99 (dd, 1H, Ar); 8.14 (d, 1H, Ar); 8,54 (s, 1H, Ar); and 10.06 (s, 1H, CHO). An infrared absorption (KBr windows) spectrum yielded the following peaks (in $cm^{-1}$): ν(C—H) 2973; 2894; 2822; 2745, ν(C—H in Ar) 3052, ν(C=O) 1682, ν(C=C, C—N in Ar) 1622; 1591; 1577; 1494; 1447; 1237, γ(Ar) 807; 749; 736. A mass spectrum yielded an ion with a mass to charge ratio of (m/z): 224 (100%, M+1).

9-Ethylcarbazole-3-carbaldehyde (10 g, 0.045 mol) was dissolved in 300 ml of methanol under mild heating. Then, a solution of 7.25 g (0.067 mol) of N-phenylhydrazine (obtained from Aldrich) in methanol was added. The reaction mixture was refluxed for 2 hours. Yellowish crystals were separated by filtration, washed with a large amount of methanol and dried. The Yield was 13.12 g (92%). The product had a melting point of 136–137° C. A $^1H$ NMR spectrum yielded the following chemical shifts (100 MHz, $CDCl_3$, δ, ppm): 1.34 (t, J=7.0 Hz, 3H, $CH_3$); 4.23 (q, J=7.0 Hz, 2H, $CH_2$); 6.90–7.64 (m, 8H, Ar); 7.60 (s, 1H, Ar); 7.81 (dd, 1H, Ar); 8.08 (d, 2H, Ar); and 8.15(d, 1H, =CH). An infrared absorption (KBr windows) spectrum yielded the following peaks (in $cm^{-1}$): ν(N—H) 3306, ν(C—H) 2972, ν(arene C—H) 3051, ν(C=C, C—N in Ar) 1602; 1494; 1475; 1237, ν(C—N) 1256, γ(Ar) 815; 747; 731. A mass spectrum yielded ions with the following mass to charge ratios (m/z): 314 (90%, M+1); 222 (100%, $H_5C_2$–$C_{12}H_7N$—CH=NH).

9-Ethylcarbazole-3-carbaldehyde-N-phenylhydrazone (10 g, 0.031 mol) was dissolved in 50 ml of ethyl methyl ketone, and then 2-chloroethyl vinyl ether (6.4 ml, 0.062 mol, obtained from Aldrich) was added to the solution. Next, 3.5 g (0.062 mol) of KOH and 4.3 g (0.031 mol) of $K_2CO_3$ were added in two portions into the reaction mixture. The reaction mixture was refluxed for 36 hours. The product was purified by column chromatography with an eluant mixture of hexane and acetone in a volume ratio of 7:1. The yield was 44.8% (5.47 g). The product had a melting point of 106–107° C. A $^1H$ NMR spectrum yielded the following chemical shifts (100 MHz, $CDCl_3$, δ, ppm): 1.40 (t, J=7.0 Hz, 3H, $CH_3$); 3.61–4.71 (m, 8H, N—$CH_2$—$CH_2$—O, N(Ar)—$CH_2$, $CH_2$=)); 6.59 (q, 1H, O—CH=); 6.90–7.60 (m, 9H, Ar); 7.79–8.32 (m, 3H, Ar); 8.35–8.45 (s,1H, CH=N). An infrared absorption (KBr windows) spectrum yielded the following peaks (in $cm^{-1}$): ν(C—H) 2971; 2921; 2880, ν(arene C—H) 3051, ν(C=C, C=N in Ar) 1616; 1592; 1494; 1480, ν(C—N) 1233; 1203, γ(Ar) 797; 749. A mass spectrum analysis yielded ions with the following mass to charge ratios (m/z): 384 (83%, M+1); 224 (100%, M-159); 120 (78%, $C_6H_5$—NH—N=$CH_2$).

Phosphorus oxychloride ($POCl_3$; 118 g, 0.77 mol) was added dropwise to 67.5 g (0.92 mol) of dry dimethylformamide (DMF) at 0° C. under nitrogen atmosphere to form a solution. The solution was warmed up slowly to the room temperature. A solution of 15 g (0.077 mol) of 9-ethylcarbazole (obtained from Aldrich) in 50 ml of dry DMF was added dropwise to the solution. The reaction mixture was heated at 80° C. for 60 hours. It was cooled and then poured into 700 ml ice water. The mixture obtained was neutralized with 10% potassium hydroxide solution until the pH reached a value of 6–8. The precipitate was separated by filtration and washed several times with hot water. The product was purified by column chromatography using an eluant mixture of hexane and ethyl acetate in a volume ratio of 3:1. The yield was 60% (11.5 g). The product had a melting point of 126–127° C. A $^1$H NMR spectrum yielded the following chemical shifts (100 MHz, CDCl$_3$, δ, ppm): 1.49 (t, J=7.0 Hz, 3H, CH$_3$); 4.41 (q, J=7.0 Hz, 2H, CH$_2$); 7.50 (d, 2H, Ar); 8.05 (d, 2H, Ar); 8.60 (s, 2H, Ar); 8.54 (s, 1H, Ar); and 10.10 (s, 2H, CHO). An infrared absorption spectrum (KBr windows) yileded the following peaks (in cm$^{-1}$): ν(C—H) 2805; 2724, ν(C—H in Ar) 3049; 2979, ν(C=O) 1682, ν(C=C in Ar) 1628; 1591; 1570; 1487, ν(C—N) 1237, γ(Ar) 828; 814. A mass spectrum analysis yielded an ion with the following mass to charge ratio (m/z): 252 (100%, M+1).

Sodium borohydride (3.82 g, 0.10 mol) was added into a solution of 8.42 g (0.0335 mol) of 9-ethyl-3,6-dihydroxymethylcarbazole in 300 ml of methanol in small portions. The reaction mixture was refluxed for 2 hours. After cooling, the reaction mixture was poured into 800 ml of ice water. The precipitated product was 9-ethylcarbazole-3-carbaldehyde-N-(vinyloxyethyl)-N-phenylhydrazone and was separated by filtration. The yield was 43.6% (3.73 g). The product had a melting point of 143–144° C. A $^1$H NMR spectrum yielded the following chemical shifts (100 MHz, DMSO-d$_6$, δ, ppm): 1.27 (s, 3H, CH$_3$); 4.31 (d, 2H, CH$_2$—N); 4.72 (s, 4H, O—CH$_2$); 5.19 (s, 2H, OH). An infrared absorption spectrum (KBr windows) yielded the following peaks (in cm$^{-1}$): ν(O—H) 3323; 3233, ν(C—H) 2976; 2871, ν(C—H in Ar) 3052, ν(C=C in Ar) 1494; 1483, ν(C—N) 1236, γ(Ar) 876; 806. A mass spectrum analysis yielded an ion with the following mass to charge ratio (m/z): 238 (100%, M−17 (OH)).

9-Ethylcarbazole-3-carbaldehyde-N-(vinyloxyethyl)-N-phenylhydrazone (1 g, 0.0026 mol) and 0.306 g (0.0012 mol) of 9-ethyl-3,6-dihydroxymethylcarbazole, both previously obtained as described above, were dissolved in 3 ml of dry tetrahydrofuran under nitrogen. Then, 1 ml of p-toluenesulfonic anhydride solution (0.5·10$^5$ mol) in dry THF was added at room temperature. The reaction mixture was stirred at 0° C. for 18 hours. Then, the THF was evaporated, and the crude product was purified by column chromatography with an eluant mixture of hexane and acetone in a volume ratio of 7:1. The yield was 19% (0.08 g). A $^1$H NMR spectrum yielded the following chemical shifts (100 MHz, CDCl$_3$, δ, ppm): 1.38 (m, 15H, CH$_3$); 4.25 (m, 18H, CH$_2$, CH); 6.80–8.65 (m, 32H, Ar, =CH—). An infrared absorption spectrum (KBr windows) yielded the following peaks (in cm$^{-1}$): ν(C—H) 2890, ν(C—H in Ar) 3049; 2974, ν(C=C in Ar) 1628; 1599; 1509; 1491, ν(C—N) 1236, γ(Ar) 803; 748.

Compound (3)

POCl$_3$ (3.8 ml, 0.0408 mol, obtained from Aldrich) was added dropwise to 4.73 ml (0.0612 mol) of dry dimethylformamide (DMF) at 0° C. under nitrogen atmosphere. The solution was warmed up slowly to room temperature. Then, a solution of 5 g (0.0204 mol) of triphenylamine (Aldrich) in 20 ml of dry DMF was added dropwise. The reaction mixture was heated at 80° C. for 24 hours and then poured into ice water. The resulting mixture was neutralized with 10% solution of potassium hydroxide until pH reached 6–8. The product was extracted with chloroform. The chloroform extract was dried with anhydrous sodium sulfate and filtered. The solvent was evaporated in a vacuum by water pump/aspirator. The product was crystallized from methanol. The yield was 5.57 g (72%). The product had a melting point of 126.5° C. A $^1$H NMR spectrum yielded the following chemical shifts (100 MHz, CDCl$_3$, δ, ppm): 6.57–7.56 (m, 12H, Ar), 7.60–7.98 (m, 2H, Ar), and 10.21 (s, 1H, CHO). An infrared absorption spectrum (KBr windows) yielded the following peaks (in cm$^{-1}$): ν(C—H) 2743; 2830, ν(C—H in Ar) 3037, ν(C=O) 1689, ν(C=C in Ar) 1585; 1567; 1490, γ(Ar) 825. A mass spectrum analysis yielded an ion with the following mass to charge ratio (m/z): 274 (100%, M+1).

Triphenylamino-4-carbaldehyde (10 g, 0.037 mol) was dissolved in 300 ml of methanol under mild heating. Then, a solution of 5.94 g (0.055 mol) of N-phenylhydrazine in 5 ml of methanol was added. The reaction mixture was refluxed for 0.5 h. Yellowish crystals were separated by filtration, washed with a large amount of methanol and dried. The yield was 11.7 g (86.7%). The product had a melting point of 168–169° C. A $^1$H NMR spectrum yielded the following chemical shifts (100 MHz, CDCl$_3$, δ, ppm): 6.55–7.64 (m, 21H, Ar, =CH, —NH). An infrared absoprtion spectrum (KBr windows) yielded the following peaks (cm$^{-1}$): ν(N—H) 3294, ν(arene C—H) 3026, ν(C=C in Ar) 1595; 1489, ν(C—N) 1282; 1257, γ(Ar) 750; 731. A mass spectrum analysis yielded an ion with the following mass to charge ratio (m/z): 364 (100%, M+1).

Triphenylamine-4-carbaldehyde-N-phenylhydrazone (10 g, 0.027 mol) was dissolved in 50 ml of ethyl methyl ketone. A 5.5 ml (0.054 mol) of 2-chloroethyl vinyl ether (obtained from Aldrich) was added to the solution, and then a mixture of 3.02 g (0.054 mol) of KOH and 3.73 g (0.027 mol) of K$_2$CO$_3$ was added in two portions into the reaction mixture. The reaction mixture was refluxed for 15 hours. The product was purified by column chromatography with an eluant mixture of hexane and acetone in a volume ratio of 7:1. The yield was 37.7% (3.5 g). The product had a melting point of 107–108° C. A $^1$H NMR (100 MHz, CDCl$_3$, δ, ppm): 3.52–4.47 (m, 6H, N—CH$_2$—CH$_2$—O, CH$_2$=)); 6.43 (q, 1H, O—CH=); 6.70–8.03 (m, 20H, Ar, CH=N). An infrared absprotion spectrum (KBr windows) yielded the following peaks (in cm$^{-1}$): ν(C—H) 2983; 2926; 2878, ν(arene C—H) 3033, ν(C=C, in Ar) 1618; 1591; 1494, ν(C—N) 1315; 1276, γ(Ar) 751; 693.

Phosphorus oxychloride (POCl$_3$, 118 g, 0.77 mol) was added dropwise to 67.5 g (0.92 mol) of dry dimethylformamide (DMF) at 0° C. under nitrogen. This solution was warmed up slowly to the room temperature. A solution of 15 g (0.077 mol) of 9-ethylcarbazole (obtained from Aldrich) in 50 ml of dry DMF was added dropwise to this solution. The reaction mixture was heated at 80° C. for 60 hours and, after cooling, poured into 700 ml of ice water. The resulting mixture was neutralized with 10% potassium hydroxide solution until pH reached a value of 6–8. The precipitate was separated by filtration and washed several times with hot water. The product was purified by column chromatography using an eluant mixture of hexane and ethyl acetate in a volume ratio of 3:1. The yield was 60% (11.5 g). The product had a melting point of 126–127° C. A $^1$H NMR spectrum yielded the following chemical shifts (100 MHz, CDCl$_3$, δ, ppm): 1.49 (t, J=7.0 Hz, 3H, CH$_3$); 4.41 (q, J=7.0 Hz, 2H, CH$_2$); 7.50 (d, 2H, Ar); 8.05 (d, 2H, Ar); 8.60 (s, 2H, Ar); 8.54 (s, 1H, Ar), and 10.10 (s, 2H, CHO). AN infrared absorption spectrum (KBr windows) yielded the following peaks (in cm$^{-1}$): ν(C—H) 2805; 2724, ν(C—H in Ar) 3049; 2979, ν(C=O) 1682, ν(C=C in Ar) 1628; 1591; 1570; 1487, ν(C—N) 1237, γ(Ar) 828; 814. A mass spectrum analysis yielded an ion with the following mass to charge ratio (m/z): 252 (100%, M+1).

Sodium borohydride (3.82 g, 0.10 mol) was added into a solution of 8.42 g (0.0335 mol) of 9-ethyl-3,6-dihydroxymethylcarbazole in 300 ml of methanol in small portions. The reaction mixture was refluxed for 2 hours. After cooling, the reaction mixture was poured into 800 ml of ice water. The precipitated product was separated by filtration. The yield was 43.6% (3.73 g). The product had a melting point of 143–144° C. A $^1$H NMR spectrum yielded the following chemical shifts (100 MHz, DMSO-d$_6$, δ, ppm): 1.27 (s, 3H, CH$_3$); 4.31 (d, 2H, CH$_2$—N); 4.72 (s, 4H, O—CH$_2$); 5.19 (s, 2H, OH). An infrared absorption spectrum (KBr windows) yielded the following peaks (in cm$^{-1}$): ν(O—H) 3323; 3233, ν(C—H) 2976; 2871, ν(C—H in Ar) 3052, ν(C=C in Ar) 1494; 1483, ν(C—N) 1236, γ(Ar) 876; 806. A mass spectrum analysis yielded an ion with the following mass to charge ratio (m/z): 238 (100%, M−17(OH)).

Triphenylamine-4-carbaldehyde-N-(vinyloxyethyl)-N-phenylhydrazone (1 g, 0.0026 mol) and 0.266 g (0.0012 mol) of 9-ethyl-3,6-dihydroxymethylcarbazole, both previously obtained as described above, were dissolved in 3 ml of dry THF under nitrogen. Then, 1 ml of p-toluenesulfonic anhydride solution in dry THF was added at room temperature. The reaction mixture was stirred at 0° C. for 24 h. Then, THF was evaporated, and the crude product was purified by column chromatography using an eluant mixture of hexane and acetone in a volume ratio of 7:1. The yield was 21% (0.09 g).

Example 2

Charge Mobility Measurements

This example describes the measurement of charge mobility for samples formed with the two charge transport materials described in Example 1.

Sample 1
A mixture of 0.1 g of Compound (2) and 0.1 g of polycarbonate Z was dissolved in 2 ml of THF. The solution was coated on a polyester film with conductive aluminum layer by the dip roller method. After drying for 15 min. at 80° C. temperature, a clear 10 μm thick layer was formed.

Sample 2
Sample 2 was prepared according to the procedure for Sample 1, except that Compound (3) was used in place of Compound (2).

Mobility Measurements
Each sample was corona charged positively up to a surface potential U and illuminated with 2 ns long nitrogen laser light pulse. The hole mobility μ was determined as described in Kalade et al., "Investigation of charge carrier transfer in electrophotographic layers of chalkogenide glasses," Proceeding IPCS 1994: The Physics and Chemistry of Imaging Systems, Rochester, N.Y., pp. 747–752, incorporated herein by reference. The hole mobility measurement was repeated with changes to the charging regime to charge the sample to different U values, which corresponded to different electric field strength inside the layer E. This dependence on electric field strength was approximated by the formula $$\mu=\mu_0 e^{\alpha\sqrt{E}}.$$

Here E is electric field strength, $\mu_0$ to is the zero field mobility and α is Pool-Frenkel parameter. The mobility characterizing parameters $\mu_0$ and α values as well as the mobility value at the 6.4×10$^5$ V/cm field strength as determined from these measurements are given in Table 1.

TABLE 1

| Sample | $\mu_0$ (cm$^2$/V · s) | μ (cm$^2$/V · s) at 6.4 × 10$^5$ V/cm | α (cm/V)$^{1/2}$ |
|---|---|---|---|
| 1 | 4 · 10$^{-10}$ | 9 · 10$^{-8}$ | 0.0069 |
| 2 | 1 · 10$^{-7}$ | 5 · 10$^{-6}$ | 0.0048 |

Example 3

Ionization Potential Measurements

This example describes the measurement of the ionization potential for the two charge transport materials described in Example 1.

To perform the ionization potential measurements, a thin layer of charge transport material with about 0.5 μm thickness was coated from a solution of 2 mg of charge transport material in 0.2 ml of tetrahydrofuran on a 20 cm$^2$ substrate surface. The substrate was polyester film with an aluminum layer over a methylcellulose sublayer of about 0.4 μm thickness.

Ionization potential was measured as described in Grigalevicius et al., "3,6-Di(N-diphenylamino)-9-phenylcarbazole and its methyl-substituted derivative as novel hole-transporting amorphous molecular materials," Synthetic Metals 128 (2002), p. 127–131, incorporated herein by reference. In particular, each sample was illuminated with monochromatic light from the quartz monochromator with a deuterium lamp source. The power of the incident light beam was 2–5·10$^{-8}$ W. A negative voltage of −300 V was supplied to the sample substrate. A counter-electrode with the 4.5×15 mm$^2$ slit for illumination was placed at 8 mm distance from the sample surface. The counter-electrode was connected to the input of a BK2-16 type electrometer, working in the open input regime, for the photocurrent measurement. A 10$^{-15}$–10$^{-12}$ amp photocurrent was flowing in the circuit under illumination. The photocurrent, I, was strongly dependent on the incident light photon energy hv. The I$^{0.5}$=f(hv) dependence was plotted. Usually, the dependence of the square root of photocurrent on incident light quanta energy is well described by linear relationship near the threshold (see references "Ionization Potential of Organic Pigment Film by Atmospheric Photoelectron Emission Analysis," *Electrophotography,* 28, Nr. 4, p. 364 (1989) by E. Miyamoto, Y. Yamaguchi, and M. Yokoyama; and "Photoemission in Solids," Topics in Applied Physics, 26, 1–103 (1978) by M. Cordona and L. Ley, both of which are incorporated herein by reference). The linear part of this dependence was extrapolated to the hv axis, and the Ip value was determined as the photon energy at the interception point. The ionization potential measurement has an error of ±0.03 eV. Table 2 lists the ionization potential values.

TABLE 2

| Compound | Ionization Potential $I_P$ (eV) |
|---|---|
| 2 | 5.30 |
| 3 | 5.41 |

As understood by those skilled in the art, additional substitution, variation among substituents, and alternative methods of synthesis and use may be practiced within the scope and intent of the present disclosure of the invention. The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

What is claimed is:

1. An organophotoreceptor comprising an electrically conductive substrate and a photoconductive element on the electrically conductive substrate, the photoconductive element comprising:

(a) a charge transport material having the formula

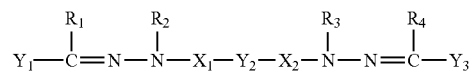

where $R_1$, $R_2$, $R_3$, and $R_4$ are, independently, H, an alkyl group, an alkaryl group, or an aryl group;

$X_1$ and $X_2$ are, independently, a linking group having the formula —$(CH_2)_m$—, branched or linear, where m is an integer between 1 and 20, inclusive, and one or more of the methylene groups is optionally replaced by O, S, C=O, O=S=O, a heterocyclic group, an aromatic group, urethane, urea, an ester group, a $NR_5$ group, a $CHR_6$ group, or a $CR_7R_8$ group where $R_4$, $R_5$, $R_6$, and $R_7$ are, independently, H, hydroxyl group, thiol group, an alkyl group, an alkaryl group, a heterocyclic group, or an aryl group; and $Y_1$, $Y_2$, and $Y_3$ are, independently, an arylamine group; and (b) a charge generating compound.

2. An organophotoreceptor according to claim 1 wherein $Y_2$ comprises a carbazole group.

3. An organophotoreceptor according to claim 2 wherein $Y_1$ and $Y_3$ comprise, independently, a carbazole group, a julolidine group, or an (N,N-disubstituted)arylamine group.

4. An organophotoreceptor according to claim 1 wherein the charge transport material has a formula selected form the group consisting of the following:

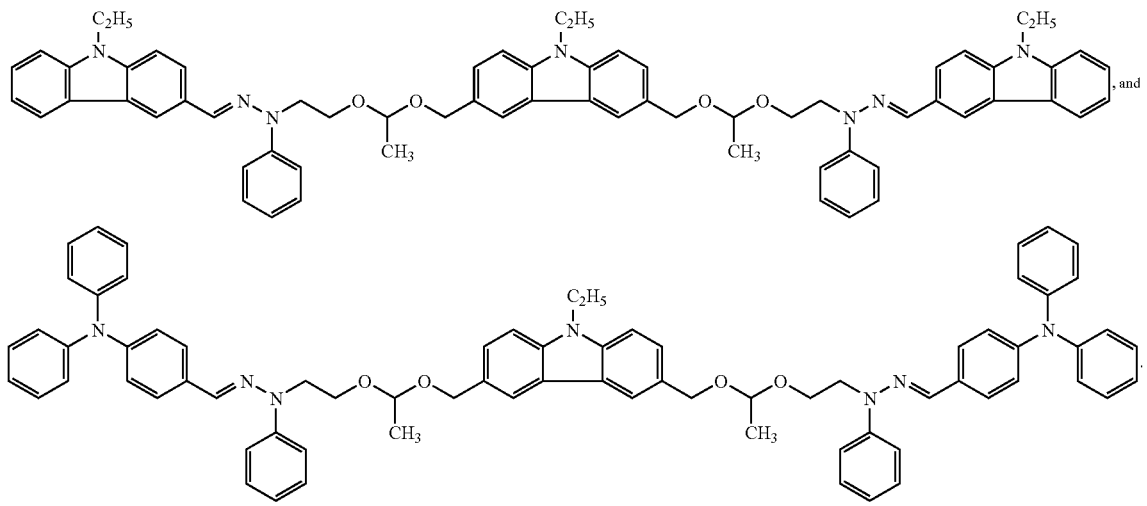

5. An organophotoreceptor according to claim 1 wherein the photoconductive element further comprises a second charge transport material.

6. An organophotoreceptor according to claim 5 wherein the second charge transport material comprises an electron transport compound.

7. An organophotoreceptor according to claim 1 wherein the photoconductive element further comprises a binder.

8. An electrophotographic imaging apparatus comprising:

(a) a light imaging component; and (b) an organophotoreceptor oriented to receive light from the light imaging component, the organophotoreceptor comprising an electrically conductive substrate and a photoconductive element on the electrically conductive substrate, the photoconductive element comprising:

(i) a charge transport material having the formula

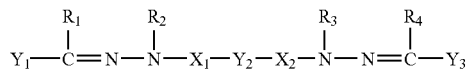

where $R_1$, $R_2$, $R_3$, and $R_4$ are, independently, H, an alkyl group, an alkaryl group, or an aryl group;

$X_1$ and $X_2$ are, independently, a linking group having the formula $—(CH_2)_m—$, branched or linear, where m is an integer between 1 and 20, inclusive, and one or more of the methylene groups is optionally replaced by O, S, C=O, O=S=O, a heterocyclic group, an aromatic group, urethane, urea, an ester group, a $NR_5$ group, a $CHR_6$ group, or a $CR_7R_8$ group where $R_4$, $R_5$, $R_6$, and $R_7$ are, independently, H, hydroxyl group, thiol group, an alkyl group, an alkaryl group, a heterocyclic group, or an aryl group; and $Y_1$, $Y_2$, and $Y_3$ are, independently, an arylamine group; and (ii) a charge generating compound.

9. An electrophotographic imaging apparatus according to claim 8 wherein $Y_2$ comprises a carbazole group.

10. An electrophotographic imaging apparatus according to claim 9 wherein $Y_1$ and $Y_3$ comprise, independently, a carbazole group, a julolidine group, or an (N,N-disubstituted)arylamine group.

11. An electrophotographic imaging apparatus according to claim 8, wherein the charge transport material has a formula selected form the group consisting of the following:

14. An electrophotographic imaging apparatus according to claim 8 further comprising a liquid toner dispenser.

15. An electrophotographic imaging process comprising;

(a) applying an electrical charge to a surface of an organophotoreceptor comprising an electrically conductive substrate and a photoconductive element on the electrically conductive substrate, the photoconductive element comprising (i) a charge transport material having the formula

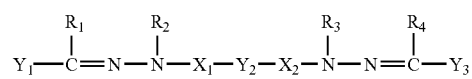

where $R_1$, $R_2$, $R_3$, and $R_4$ are, independently, H, an alkyl group, an alkaryl group, or an aryl group;

$X_1$ and $X_2$ are, independently, a linking group having the formula $—(CH_2)_m—$, branched or linear, where m is an integer between 1 and 20, inclusive, and one or more of the methylene groups is optionally replaced by O, S, C=O, O=S=O, a heterocyclic group, an aromatic group, urethane, urea, an ester group, a $NR_5$ group, a $CHR_6$ group, or a $CR_7R_8$ group where $R_4$, $R_5$, $R_6$, and $R_7$ are, independently, H, hydroxyl group, thiol group, an alkyl group, an alkaryl group, a heterocyclic group, or an aryl group; and $Y_1$, $Y_2$, and $Y_3$ are, independently, an arylamine group; and (ii) a charge generating compound, (b) imagewise exposing the surface of the organophotoreceptor to radiation to dissipate charge in selected areas and thereby form a pattern of charged and uncharged areas on the surface;

(c) contacting the surface with a toner to create a toned image; and

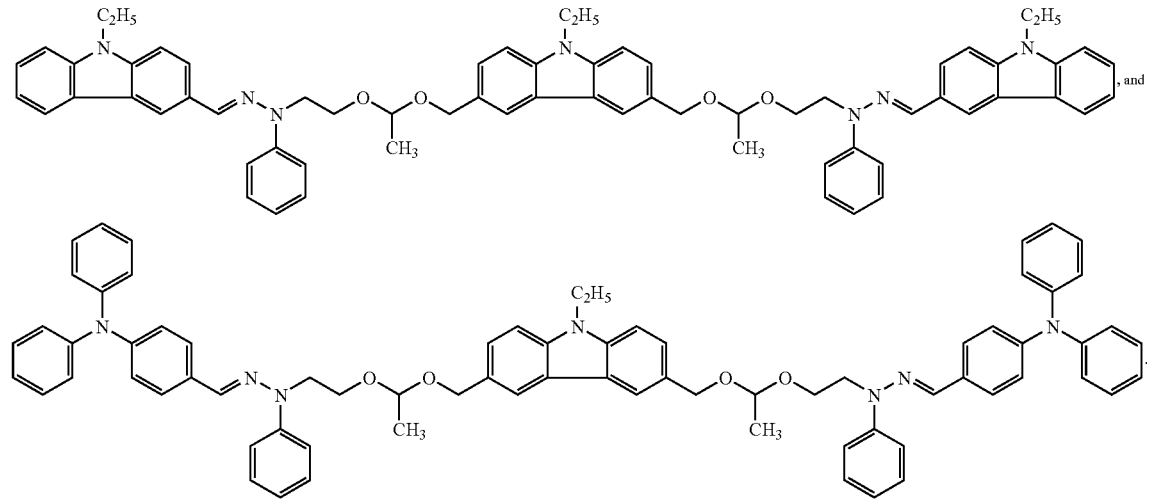

12. An electrophotographic imaging apparatus according to claim 8 wherein the photoconductive element further comprises a second charge transport material.

13. An electrophotographic imaging apparatus according to claim 12 wherein second charge transport material comprises an electron transport compound.

(d) transferring the toned image to substrate.

16. An electrophotographic imaging process according to claim 15 wherein $Y_2$ comprises a carbazole group.

17. An electrophotographic imaging process according to claim 16 wherein $Y_1$ and $Y_3$ coprise, independently, a carbazole group, a julolidine group, or an (N,N-disubstituted) arylamine group.

18. An electrophotographic imaging process according to claim 15 wherein the charge transport material has a formula selected from the group consisting of the following:

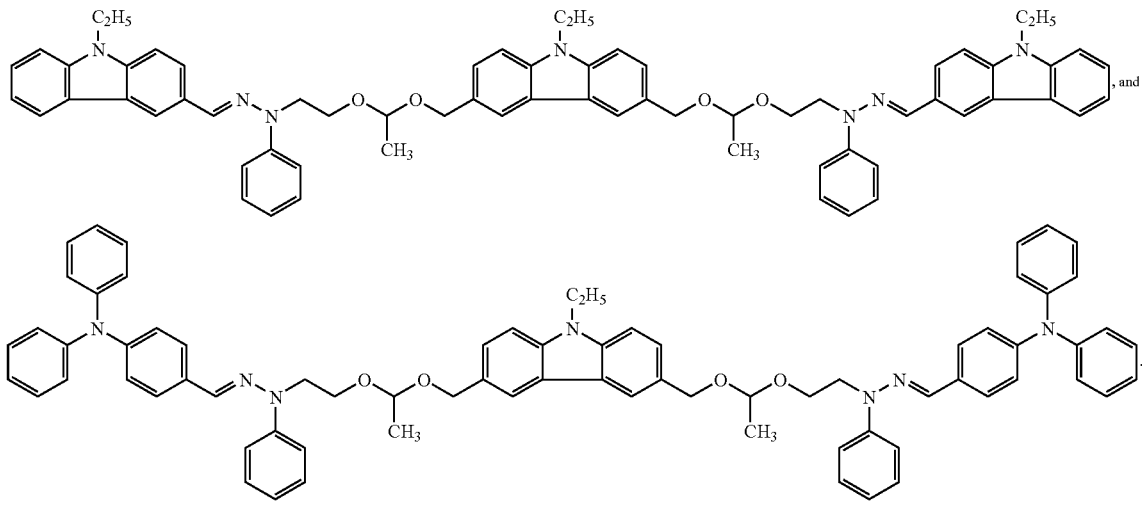

19. An electrophotographic imaging process according to claim 15 wherein the photoconductive element further comprises a second charge transport material.

20. An electrophotographic imaging process according to claim 19 wherein the second charge transport material comprises an electron transport compound.

21. An electrophotographic imaging process according to claim 15 wherein the photoconductive element further comprises a binder.

22. An electrophotographic imaging process according to claim 15 wherein the toner comprises a liquid toner comprising a dispersion of colorant particles in an organic liquid.

23. A charge transport material having the formula:

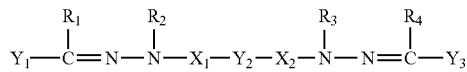

where $R_1$, $R_2$, $R_3$, and $R_4$ are, independently, H, an alkyl group, an alkaryl group, or an aryl group;

$X_1$ and $X_2$ are, independently, a linking group having the formula $-(CH_2)_m-$, branched or linear, where m is an integer between 1 and 20, inclusive, and one or more of the methylene groups is optionally replaced by O, S, C=O, O=S=O, a heterocyclic group, an aromatic group, urethane, urea, an ester group, a $NR_5$ group, a $CHR_6$ group, or a $CR_7R_8$ group where $R_4$, $R_5$, $R_6$, and $R_7$ are, independently, H, hydroxyl group, thiol group, an alkyl group, an alkaryl group, a heterocyclic group, or an aryl group; and $Y_1$, $Y_2$, and $Y_3$ are, independently, an arylamine group.

24. A charge transport material according to claim 23 wherein $Y_2$ comprises a carbazole group.

25. A charge transport material according to claim 24 wherein $Y_1$ and $Y_3$ comprise, independently, an arylamine group selected from the group consisting of a carbazole group, a julolidine group, a julolidine group, or an (N,N-disubstituted)arylamine group.

26. A charge transport material according to claim 23 wherein the charge transport material has a formula selected from the group consisting of the following:

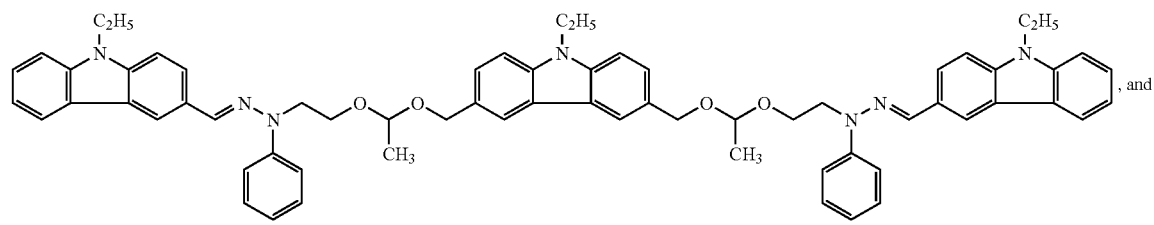

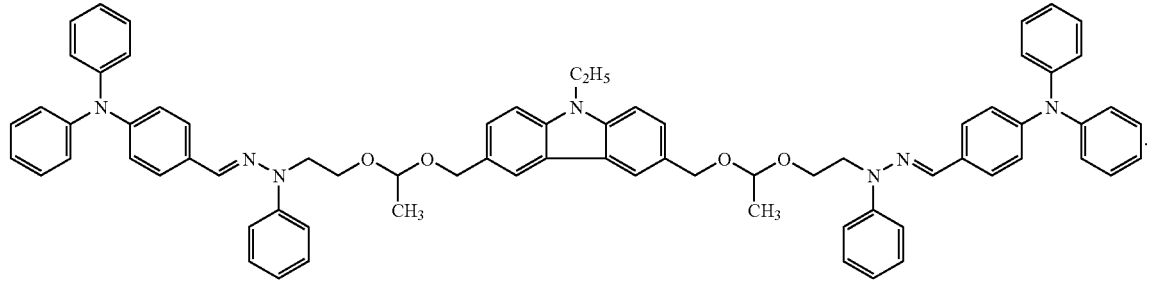
* * * * *